United States Patent [19]

Onopchenko et al.

[11] 3,993,676

[45] Nov. 23, 1976

[54] OXIDATION OF ALKANES

[75] Inventors: Anatoli Onopchenko, Monroeville; Johann G. D. Schulz, Pittsburgh, both of Pa.

[73] Assignee: Gulf Research & Development Company, Pittsburgh, Pa.

[22] Filed: June 2, 1975

[21] Appl. No.: 582,728

Related U.S. Application Data

[63] Continuation-in-part of Ser. No. 134,886, April 16, 1971, abandoned.

[52] U.S. Cl. ............................. 260/413; 260/533 R
[51] Int. Cl.$^2$ ........................................ C07C 51/14
[58] Field of Search ...................... 260/413, 533 R

[56] References Cited

UNITED STATES PATENTS

| 2,675,407 | 4/1954 | Gallo et al. .......................... 260/533 |
| 3,196,182 | 7/1965 | Cox ................................... 260/533 R |
| 3,646,078 | 2/1972 | Fanning .............................. 260/413 |

*Primary Examiner*—Winston A. Douglas
*Assistant Examiner*—P. E. Konopka

[57] ABSTRACT

A process for converting substantially all of an alkane to a product predominating in carboxylic acids of lesser carbon numbers which comprises heating a mixture of an alkane and acetic acid, while stirring, with molecular oxygen in the absence of a heavy metal catalyst.

5 Claims, No Drawings

OXIDATION OF ALKANES

This application is a continuation-in-part application of our U.S. Patent Application Ser. No. 134,886, entitled OXIDATION OF ALKANES, filed Apr. 16, 1971, now abandoned which application is hereby incorporated in by reference.

BACKGROUND OF THE INVENTION

1. Field of the Invention

This invention relates to a process for converting an alkane to carboxylic acids by subjecting said alkane to the action of molecular oxygen in the presence of acetic acid but in the absence of a heavy metal oxidation catalyst.

2. Description of the Prior Art

The oxidation of an alkane with molecular oxygen to obtain carboxylic acids selectively has been difficult. Luther et al in U.S. Pat. No. 1,864,079 have oxidized an alkane in the presence of from two to 20 percent of a lower acid, such as formic acid, acetic acid or propionic acid, or mixtures thereof, preferably in the presence of an oxidation catalyst, to obtain a product predominating in alcohols, which, in turn, react with said lower acid to form the corresponding esters thereof. Fanning, in Canadian Pat. No. 773,592, states that such oxidation is difficult, that the same cannot be carried out in the presence of acetic acid, even when a heavy metal catalyst is employed, and that these difficulties can be avoided when the alkane is oxidized in a system containing a combination of acetic and propionic acids, because this mixture serves to maintain a single-phase system. In U.S. Pat. No. 3,196,182 Cox is interested in oxidizing a lower hydrocarbon, such as butane, in a manner so as to obtain higher ratios of methyl ethyl ketone to acetic acid by contacting the hydrocarbon with an oxygen-containing gas in the presence of a liquid recycle medium and/or a normally liquid organic vehicle, which serves to maintain the hydrocarbon in essentially liquid phase, in an elongated reaction zone while eliminating backmixing, thus establishing a flow pattern that he characterizes as "plug flow".

SUMMARY OF THE INVENTION

We have found that selected alkanes can easily be converted to a product predominating in carboxylic acids (alkanoic acids) having carbon numbers lower than said alkane charge by heating while stirring, said alkane with molecular oxygen in the presence of acetic acid but in absence of a heavy metal catalyst. In other words the necessary components in our charge consist essentially of the alkane, acetic acid and molecular oxygen. This is surprising in view of the above, because the present reaction system is a two-phase system, and with the production of water during the oxidation remains a two-phase system throughout the reaction period. In addition, surprisingly, a heavy metal catalyst is detrimental but the water of reaction, which can be allowed to remain in the reaction system as it is formed, is not detrimental.

The present process requires but three components: an alkane, acetic acid and molecular oxygen. The alkane that is employed can be defined as one having from 11 to 120 carbon atoms, preferably from 12 to 32 carbon atoms, most preferably from 14 to 20 carbon atoms. Specific examples of such alkanes are normal and iso alkanes of the following: undecane, dodecane, tridecane, tetradecane, pentadecane, hexadecane, heptadecane, octadecane, nonadecane, eicosane, heneicosane, docosane, tricosane, tetracosane, pentacosane, hexacosane, heptacosane, octacosane, nonacosane, triacontane, hentriacontane, dotriacontane, tritriacontane, tetratriacontane, pentatriacontane, hexatriacontane, heptatriacontane, octatriacontane, nonatriacontane, tetracontane, pentacontane, hexacontane, heptacontane, octacontane, nonacontane, decacontane, 2,2-dimethyldecacontane, 3,3-methylethyldecacontane, 4,4-methylphenyldecacontane, 4-ethyl-4-(2,4-dimethylphenyl) decacontane, 2,2,4,4-tetramethylcosane, 1,1-dimethyl-5,5-diethylcyclooctane, 2,3,4,5-tetramethylheptane, 2-methyl-3-cyclohexylpentane, dicyclohexylmethane, hexylcycloheptane, heptylcyclooctane, decylcyclohexane, 2-methyl-3-ethylpentane, 3,3-diethylhexane, 1,3,5,7-tetramethylcyclooctane, methylcyclodecane, cyclododecane, etc. The ratio of alkane to acetic acid is critical and must be, on a weight basis, from about 5:1 to about 0.5:1, preferably from about 3:1 to about 1:1. The amount of molecular oxygen needed is the amount stoichiometrically required to react with the alkane and to convert the same to the desired carboxylic acids. A large excess of oxygen is generally required to maintain the operating pressure.

The reaction conditions are relatively mild, with the temperature being of the order of about 100° to about 200° C., preferably from about 120° to about 145° C., and the pressure about 50 to about 500 pounds per square inch gauge, preferably about 100 to about 250 pounds per square inch gauge. The reaction time is a function of conversion desired. In general, the time can be from about ½ hour to about 48 hours, but, in general, a reaction time of about 2 to about 10 hours will suffice to convert substantially all of the alkane to desired carboxylic acids.

DESCRIPTION OF PREFERRED EMBODIMENTS

The process herein can further be illustrated by the following.

EXAMPLE I

A series of runs was made in a 1-liter, 316-stainless steel, magnetically-stirred autoclave. The reactants were charged to the autoclave, oxygen was introduced therein at a rate of about 0.6 cubic feet per hour, which was sufficient to maintain a pressure of 175 psig (12.4 kg/cm$^2$) throughout the reaction period of six hours, and the reaction temperature was maintained at 135° C. During the reaction vent gases, which included oxygen, carbon monoxide, carbon dioxide and traces of gaseous hydrocarbon, were removed through a vent with which the autoclave was provided. Water of reaction was permitted to remain in the reactor throughout the reaction period. At the end of the reaction the autoclave was cooled to room pressure, depressured through a series of traps and its contents removed. The work-up of the crude mixture, by simple distillation under reduced pressure to minimize the formation of tars by decomposing various products on prolonged exposure to heat, was sufficient to remove acetic acid, both solvent and product, traces of propionic acid and butyric acids as well as water from the higher-boiling materials. Extraction of the residue with water removed substantially all of the dibasic acids therein. The latter were then recovered from the extract by evaporation of water in a rotary evaporator. Separation of the $C_5$ to $C_{16}$ carboxylic acids was accomplished by vacuum distillation in cases wherein essentially complete conversion of alkane was obtained or by extraction with sodium or potassium hydroxide, followed by treatment with hydrochloric acid and distillation of the organic layer into desired carboxylic acid fractions. The remainder, containing unreacted alkane and higher-boiling oxygenated materials, such as ketones, were returned to the autoclave for recycle. The results obtained are tabulated below in TABLE I.

Despite the fact that the charge and the reaction mixture herein is a two-phase system, it can be seen from Runs Nos. 1, 5 and 6 that the results obtained are as good as those obtained in Run No. 7 wherein a mixture of both acetic and propionic acids was used as a mutual solvent. Note that in each case excellent conversions and productivity of carboxylic acids were realized while maintaining a low production of intermediate

TABLE I

| Run Number | 1 | 2 | 3 | 4 | 5 | 6 | 7 |
|---|---|---|---|---|---|---|---|
| Charge in Grams | | | | | | | |
| Cetane | 271 | 410 | 306 | 273 | 253 | 113 | 237 |
| Acetic Acid | 136 | — | — | 61 | 113 | 309 | 71 |
| Water | — | — | 100 | — | — | — | — |
| Benzene | — | — | — | 123 | 113 | — | — |
| Propionic Acid | — | — | — | — | — | — | 131 |
| Product in Grams | | | | | | | |
| Mono $C_2$ to $C_4$ Acids Produced | 91 | 54 | 35 | 32 | 65 | 119 | 251 |
| Mono $C_5$ to $C_{16}$ Acids Produced | 161 | 104 | 88 | 100 | 132 | Grams of Total Acids | Grams of Total Acids |
| Dicarboxylic Acids Produced | 74 | 19 | 32 | 27 | 50 | Acids | Acids |
| Intermediate Oxygenated Material (Ketones Alcohols, Esters, etc.) Produced | 23 | 86 | 50 | 41 | 34 | 20 | 45 |
| Yield Data | | | | | | | |
| Weight Per Cent Hydrocarbon Converted | >98 | 46 | 72 | 60 | 88 | 100 | 98 |
| Productivity of Carboxylic Acids (Grams of Carboxylic Acids Produced Per Gram of Hydrocarbon Charged) | 1.2 | 0.6 | 0.5 | 0.6 | 1.0 | 1.1 | 1.1 |
| Productivity of Intermediates (Grams of Intermediate Oxygenated Materials Produced Per Gram of Hydrocarbon Charged) | 0.1 | 0.3 | 0.2 | 0.2 | 0.1 | 0.2 | 0.2 |

Analysis by vapor phase chromatography was made of the monobasic acid and dibasic acid contents of the products produced herein. Those of Run No. 1, which are typical, are presented below in TABLES II and III.

TABLE II

| $C_4$ to $C_{16}$ Monobasic Carboxylic Acids | |
|---|---|
| Carbon Number | Weight Per Cent |
| 4 | 1.4 |
| 5 | 7.7 |
| 6 | 12.4 |
| 7 | 14.3 |
| 8 | 13.6 |
| 9 | 11.9 |
| 10 | 10.6 |
| 11 | 8.9 |
| 12 | 7.9 |
| 13 | 6.7 |
| 14 | 3.2 |
| 15 | 1.4 |
| 16 | Trace |

TABLE III

| | Dibasic Acids |
|---|---|
| Acid | Weight Per Cent |
| Oxalic | Trace |
| Malonic | Trace |
| Succinic | 55.3 |
| Glutaric | 22.7 |
| Adipic | 12.8 |
| Pimelic | 6.2 |
| Suberic | 3.0 |

Although specific analysis of the carboxylic acids in Runs Nos. 6 and 7 were not made as in the remaining runs, the distribution pattern was similar thereto.

The advantages of operating in accordance with our process is apparent from a study of the above data.

oxygenated products. With no acetic acid in Run No. 2 conversion of hydrocarbon and productivity of carboxylic acid was severely reduced and productivity of intermediates increased. The presence of water in Run No. 3 increased conversion over Run No. 2 but did not significantly alter productivity of carboxylic acids and intermediates. Runs Nos. 4 and 5 show that other solvents, such as benzene, can be present without adversely affecting the distribution of product obtained, provided acetic acid within the defined limits is also present.

That, surprisingly, a heavy metal catalyst is detrimental in the claimed process is apparent from EXAMPLES II and III below.

EXAMPLE II

Using the same autoclave and the same procedure described in EXAMPLE I, the autoclave was charged with 272.7 grams of cetane and 140.7 grams of glacial acetic acid. A total of 583.8 grams of product was obtained, an increase of about 170 grams over the initial charge. The conversion of the alkane was essentially complete, the productivity of carboxylic acids (grams of acids produced per gram of hydrocarbon charge) was 1.2:1 and the productivity of oxygenated intermediates (grams of intermediates formed per gram of hydrocarbon charge) was 0.1:1

EXAMPLE III

When the run of EXAMPLE II was repeated with 272.5 grams of cetane, 136.2 grams of glacial acetic acid and 6.2 grams of cobaltous acetate tetrahydrate, a total of 424.6 grams of product was obtained, an increase of only 15.9 grams over the initial charge. This represented a conversion of less than 10 percent of the cetane charge. Productivity of carboxylic acids and oxygenated intermediates was similar to that of EXAMPLE II.

EXAMPLE IV

Another series of runs was carried out following the procedure of Example I but using the following hydrocarbons in the charge: a mixture of $C_{14}$ to $C_{16}$ alkanes (Run No. 8) normal heptane (Run No. 9), normal decane (Run No. 10), normal tridecane (Run No. 11) and normal tetradecane (Run No. 12). The results obtained are tabulated below in TABLE IV.

TABLE IV

| Run No. | 8 | 9 | 10 | 11 | 12 |
|---|---|---|---|---|---|
| Charge in Grams | | | | | |
| Hydrocarbon | 272 Grams of a Mixture of Hydrocarbons, * | 270 Grams of N-Heptane | 270 Grams of N-Decane | 190 Grams of N-Tridecane | 260 Grams of N-Tetradecane |
| Acetic Acid | 137 | 135 | 135 | 135 | 135 |
| Product in Grams | | | | | |
| Total acids Produced of Lower Carbon Number than Charge | 310 | 105.5 | 86.6 | 146.9 | 219.8 |
| Intermediate oxygenated Materials (Ketones, Alcohols, Esters) | 48 | Not Determined | 28 | 35 | 43 |
| Yield Data | | | | | |
| Weight Per Cent Hydrocarbon Converted | >98 | 39 | 37 | 83 | >98 |
| Productivity of Carboxylic Acids (Grams of Carboxylic Acids Produced Per Gram of Hydrocarbon Charged) | 1.1 | 0.4 | 0.3 | 0.8 | 0.9 |
| Productivity of Intermediates (Grams of Intermediate Oxygenated Materials Produced Per Gram of Hydrocarbon Charged) | 0.2 | Not Determined | 0.1 | 0.2 | 0.2 |

* 131.2 grams of n-tetradecane, 88.3 grams of pentadecane, 35.5 grams of hexadecane and 16.7 grams of normal hydrocarbons lower than $C_{14}$ and higher than $C_{16}$.

The data in Table IV show that in order to obtain exceedingly high productivity of carboxylic acids per gram of hydrocarbon charged the number of carbon atoms in the hydrocarbon charge is critical. Note that in Runs Nos. 9 and 10, wherein the hydrocarbon charge was n-heptane and n-decane, respectively, the productivity of carboxylic acids (alkanoic acids) was extremely low. In Run No. 11, wherein the charge was n-tridecane the productivity was at least double that obtained in Runs Nos. 9 and 10. This increase was maintained in Run No. 12 with n-tetradecane and even further increased in Run No. 8 wherein a mixture of hydrocarbons predominating in carbon numbers within the defined range was employed.

EXAMPLE V

In this experiment commercially-available paraffin wax was used as the feed stock for producing the desired acids herein (melting point, 52°–53° C., refractive index, $n_D^{80}$, of 1.4272, having the following carbon number distribution: C-22, 7.2 weight percent; C-23, 10.8 weight percent; C-24, 12.8 weight percent; C-25, 13.2 weight percent; C-26, 10.8 weight percent; C-27, 7.8 weight percent; C-28, 5.4 weight percent; C-29, 3.7 weight percent; C-30, 2.9 weight percent; and >C-30 & <C-22, 25.4 weight percent; (average~$C_{25}$)). Prior to oxidation, this wax was dissolved in hot n-hexane and extracted three times with about 10 weight percent sodium hydroxide solution to remove inhibitor used for stabilizing the wax. The organic layer was washed with water two times and then evaporated to dryness in a rotary evaporator to obtain an inhibitor-free wax. A total of 165 grams of the above wax and 140 grams of acetic acid were charged into a standard autoclave, and brought to the operating conditions of temperature (135° C.) and pressure (175 pounds per square inch gauge or 12.4 kilograms per square centimeter). As soon as the desired conditions were reached, a momentary temperature rise to 155° C. occurred. The reactor was stabilized at 135°, however, and reaction was continued for a period of 3 hours. The autoclave was cooled, depressured, and its content of 378.2 grams of reaction product withdrawn. The product was combined with 8.3 grams of material in the traps and diluted with about three-fold volume of water to separate any unreacted wax floating on the surface, but no wax was found, indicating complete conversion to products. On work-up as before, 120 grams of $C_8$ to $C_{18}$ carboxylic acids were formed along with 35 grams of lower carboxylic acids. The distribution of the high boiling acids was as follows: C-8, 7.5 weight percent; C-9, 10.6 weight percent; C-10, 20.3 weight percent; C-11, 23.1 weight percent; C-12, 10.8 weight percent; C-13, 4.8 weight percent; C-14, 4.3 weight percent; C-15, 4.3 weight percent; C-16, 8.8 weight percent; C-17, 5.5 weight percent; and C-18, trace. The distribution of the lower acids was as follows: C-2, 52 weight percent; C-3, 29.1 weight percent; C-4, 4.7 weight percent; C-5, 3.1 weight percent; C-6, 5.1 weight percent; and C-7, 6.0 weight percent; C-8, trace. No attempt was made to determine the amount of dicarboxylic acids formed in this run. Accordingly, there was obtained a productivity of at least 0.94 grams of carboxylic acid per gram of wax charged.

Obviously, many modifications and variations of the invention, as hereinabove set forth, can be made without departing from the spirit and scope thereof, and therefore only such limitations should be imposed as are indicated in the appended claims.

We claim:
1. A process for converting an alkane having from 11 to 120 carbon atoms to a product predominating in carboxylic acids of lesser carbon numbers which consists essentially in heating, while stirring, a charge mixture consisting essentially of an alkane, acetic acid and molecular oxygen, wherein said alkane and said acetic acid are present in a weight ratio of about 3:1 to about

1:1, in a temperature range of about 100° to about 200° C. in the absence of a heavy metal catalyst, and wherein said oxygen is introduced sufficient to maintain a pressure of about 100 p.s.i.g. to about 250 p.s.i.g.

2. The process of claim 1 wherein said alkane has from 12 to 32 carbon atoms.

3. The process of claim 1 wherein said alkane has from 14 to 20 carbon atoms.

4. The process of claim 1 wherein said temperature is in the range of about 120° to about 145° C.

5. The process of claim 1 wherein the water of reaction is permitted to remain in the reaction zone throughout the reaction period.

* * * * *